(12) United States Patent
Hirose et al.

(10) Patent No.: US 7,811,802 B2
(45) Date of Patent: Oct. 12, 2010

(54) LIPASE POWDER COMPOSITION AND A PROCESS FOR PREPARING AN ESTERIFIED COMPOUND BY USING THE SAME

(75) Inventors: Tadashiro Hirose, Yokosuka (JP); Yuri Arai, Yokosuka (JP); Satoshi Negishi, Yokosuka (JP)

(73) Assignee: The Nisshin OilliO Group, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 11/703,219

(22) Filed: Feb. 7, 2007

(65) Prior Publication Data

US 2007/0141692 A1 Jun. 21, 2007

Related U.S. Application Data

(63) Continuation of application No. PCT/JP2005/014936, filed on Aug. 16, 2005.

(30) Foreign Application Priority Data

Aug. 24, 2004 (JP) ............................... 2004-243895
Mar. 28, 2005 (JP) ............................... 2005-091881

(51) Int. Cl.
*C12N 9/20* (2006.01)
*C12P 7/64* (2006.01)

(52) U.S. Cl. ...................................... 435/198; 435/134

(58) Field of Classification Search ....................... None
See application file for complete search history.

(56) References Cited

U.S. PATENT DOCUMENTS

| 4,394,445 | A | 7/1983 | Nix et al. | |
|---|---|---|---|---|
| 5,480,787 | A | 1/1996 | Negishi et al. | |
| 2003/0185939 | A1* | 10/2003 | Nielsen | ................. 426/61 |
| 2003/0199069 | A1* | 10/2003 | Fuglsang et al. | ............ 435/198 |
| 2004/0082056 | A1* | 4/2004 | Jump et al. | ................. 435/263 |

FOREIGN PATENT DOCUMENTS

| JP | 55-159794 | A | 12/1980 |
|---|---|---|---|
| JP | 60-98984 | A | 6/1985 |
| JP | 61-202688 | A | 9/1986 |
| JP | 01-262795 | A | 10/1989 |
| JP | 02-138986 | A | 5/1990 |
| JP | 03-061485 | A | 3/1991 |
| JP | 07-079789 | A | 3/1995 |
| JP | 2668187 | B2 | 7/1997 |
| JP | 2000-106873 | A | 4/2000 |
| JP | 2004-283043 | A | 10/2004 |

OTHER PUBLICATIONS

Sharma et al. (2001) Biotechnology Advances 19(8): 627-662.*
Satoshi Negishi et al., "Activation of powdered lipase by cluster water and the use of lipase powders for commercial esterification of food oils", Enzyme and Microbial Technology, Jan. 2, 2003, pp. 66-70, vol. 32, No. 1, XP002456965, ISSN:0141-0229 Elsevier Science Inc.
A. Mustranta et al., "Applications of immobilized lipases to transesterification and esterification reactions in nonaqueous systems", Enzyme and Microbial Technology, Feb. 1993, pp. 133-139, vol. 15, No. 2, XP002456966, 1SSN:0141-0229, Butterworth-Heinemann.

* cited by examiner

*Primary Examiner*—Lisa J Hobbs
(74) *Attorney, Agent, or Firm*—Buchanan Ingersoll & Rooney PC

(57) ABSTRACT

There is provided a lipase composition comprising (a) a powdered lipase which is a lipase derived from *Rhizomucor* sp. or a powdered lipase which is a lipase derived from *Penicillium* sp. and (b) a powdered lipase selected from the group consisting of a powdered lipase which is a lipase derived from *Alcaligenes* sp., a powdered lipase which is a lipase derived from *Rhizopus* sp. and a powdered lipase which is a lipase derived from *Thermomyces* sp. When using this lipase composition, a compound(s) having at least one alcoholic hydroxyl group in the molecule can be effectively esterified with a carboxylic acid(s).

9 Claims, 1 Drawing Sheet

LIPASE POWDER COMPOSITION AND A PROCESS FOR PREPARING AN ESTERIFIED COMPOUND BY USING THE SAME

TECHNICAL FIELD OF THE INVENTION

The present invention relates to a powdered lipase composition which can be suitably used in an esterification of a compound(s) having alcoholic hydroxyl group, such as glycerin, with various fatty acids and the like, and to a process for preparing an esterified compound, such as triglyceride, by using the same.

BACKGROUND OF THE INVENTION

Lipases are widely used in the reactions such as esterification of various carboxylic acids such as fatty acids with alcohols such as mono-alcohol and polyalcohol, and trans-esterification between plural carboxylates. Among these, when a lipase powder itself is used in esterification involving dehydrogenation, its activity does not fully express. Further, it is difficult to uniformly disperse the lipase powder into a reaction system, and also to recover it. Therefore, it is common to immobilize a lipase to some carriers, such as anion-exchange resin (Patent Literature 1), phenol adsorption resin (Patent Literature 2), a hydrophobic carrier (Patent Literature 3), cation-exchange resin (Patent Literature 4) and chelate resin (Patent Literature 5) and the like to use it in the reactions such as esterification reaction.

As mentioned above, a lipase has been conventionally immobilized and used in the esterification reaction. However, the immobilized lipase loses an original lipase activity through the immobilization. In addition, when a porous carrier was used, the raw materials and products have gotten stuck in fine pores and, as a result, the ratio of esterification decreases.

In light of the situations mentioned above, various technologies have been developed wherein a lipase powder is used. For example, a trans-esterification method is proposed wherein in the presence or absence of an inactive organic solvent(s), a lipase powder is dispersed into a raw material(s) containing ester in the trans-esterification in such a manner that 90% or more of the particles of the dispersed lipase powder can keep particle size of 1 to 100 μm in the reaction (Patent Literature 6). It is also proposed that enzyme powder is used, which is obtained by drying an enzyme solution(s) containing phospholipid and lipid-soluble vitamins (Patent Literature 7).

[Patent Literature 1] Japanese Patent Publication No. Sho 60-98984

[Patent Literature 2] Japanese Patent Publication No. Sho 61-202688

[Patent Literature 3] Japanese Patent Publication No. Hei 2-138986

[Patent Literature 4] Japanese Patent Publication No. Hei 3-61485

[Patent Literature 5] Japanese Patent Publication No. Hei 1-262795

[Patent Literature 6] Japanese Patent No. 2668187

[Patent Literature 7] Japanese Patent Publication No. 2000-106873

DISCLOSURE OF THE INVENTION

An object of the present invention is to provide a powdered lipase composition which allows to effectively conduct an esterification reaction.

Another object of the present invention is to provide a process for preparing an esterified compound by using the above-mentioned lipase composition.

The above objects and other objects will be apparent from the following descriptions.

By using a combination of particular two powdered lipases in place of an immobilized lipase, extremely high ratio of esterification can be accomplished, by which the above-mentioned problems can be solved. The present invention has been completed on the basis of these findings.

Namely, the present invention provides a lipase composition comprising (a) a powdered lipase which is a lipase derived from *Rhizomucor* sp. or a powdered lipase which is a lipase derived from *Penicillium* sp. and (b) a powdered lipase selected from the group consisting of a powdered lipase which is a lipase derived from *Alcaligenes* sp., a powdered lipase which is a lipase derived from *Rhizopus* sp. and a powdered lipase which is a lipase derived from *Thermomyces* sp.

The present invention also provides a process for preparing an esterified compound(s), which comprises esterifying a compound(s) having at least one alcoholic hydroxyl group in the molecule, in the presence of the above-mentioned lipase composition, with a carboxylic acid(s).

BEST MODE FOR CARRYING OUT THE INVENTION

Figure 1:
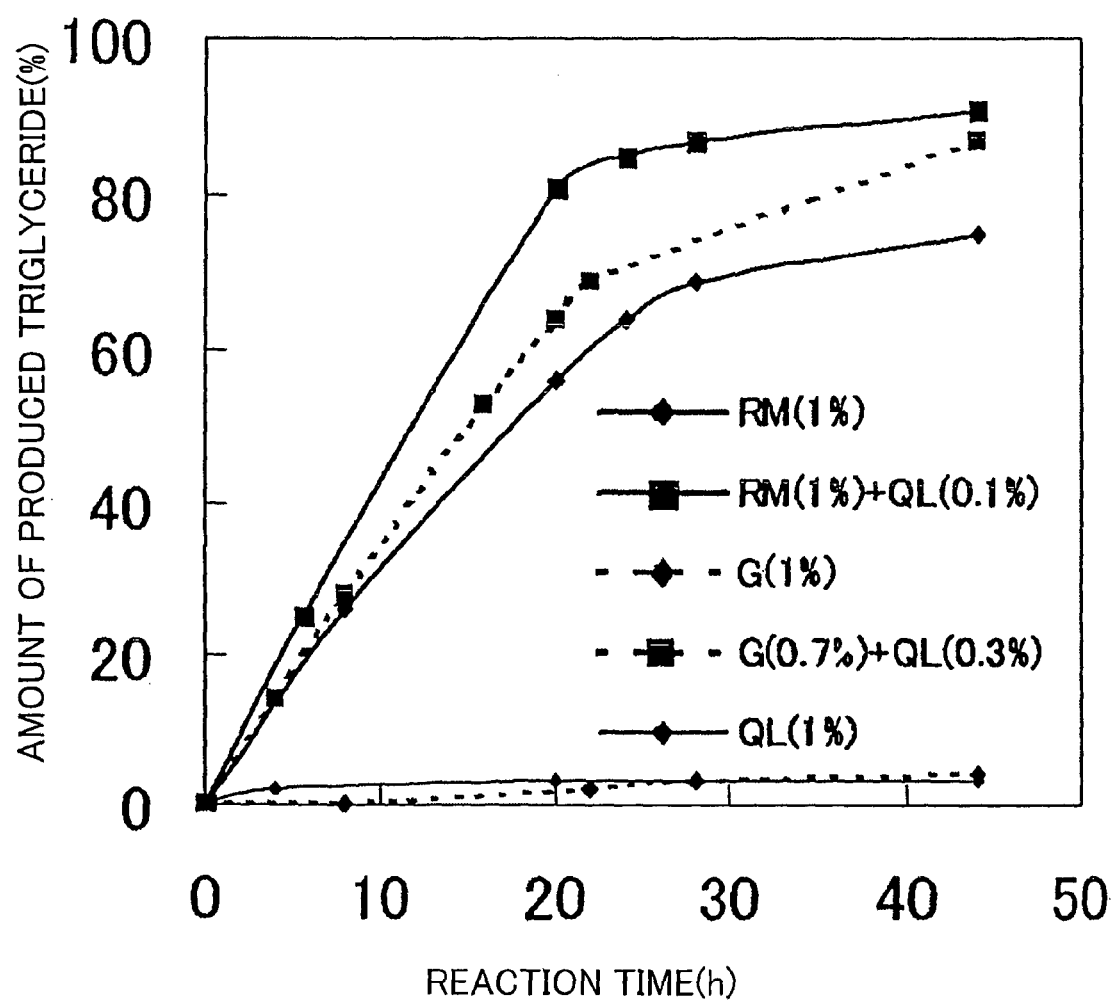
FIG. 1 demonstrates production of triglyceride in esterification reaction when the lipase composition comprising a combination of two lipases (RM (1%)+QL (0.1%) as well as G (0.7%)+QL (0.3%)).

As the lipase derived from *Rhizomucor* sp. which is used as component (a), a lipase derived from *Rhizomucor miehei*, that is, a 1,3-specific lipase is preferably used. A lipase-containing solution, Palatase (20000 L) prepared by Novozymes Japan Co., Ltd. can be made in power form to use the resultant as the powdered lipase. As this powdered lipase, a powder which is spherical and has a water content of not more than 10% by weight is preferably used. It is more preferable that the water content thereof be 6.5 to 8.5% by weight. Heretofore, *Rhizomucor miehei* sometimes used to belong to *Mucor* sp.

The above-mentioned powdered lipase can be easily prepared, for example, by spray drying an aqueous solution containing a lipase.

Here, examples of the aqueous solution containing a lipase include a lipase culture solution from which a cell body is removed, a purified culture solution thereof, a solution in which the lipase powder obtained from these culture solutions is dissolved and dispersed again; a solution in which the commercially available lipase powder is dissolved and dispersed again; and a commercially available liquid lipase. In order to enhance lipase activity, it is more preferable that low-molecular-weight components such as salts are removed from the solution. In order to enhance the powder property, it is more preferable that low-molecular-weight components such as sugar are removed from the solution.

A lipase culture solution includes, for example, aqueous solutions containing soybean flour, peptone, corn steep liquor, $K_2HPO_4$, $(NH_4)_2SO_4$, $MgSO_4 \cdot 7H_2O$ and the like. The concentrations thereof are as follows: the soybean flour is 0.1 to 20% by weight and preferably 1.0 to 10% by weight; peptone is 0.1 to 30% by weight and preferably 0.5 to 10% by weight; the corn steep liquor is 0.1 to 30% by weight and preferably 0.5 to 10% by weight; $K_2HPO_4$ is 0.01 to 20% by weight and preferably 0.1 to 5% by weight; $(NH_4)_2SO_4$ is 0.01 to 20% by weight and preferably 0.05 to 5% by weight; and $MgSO_4 \cdot 7H_2O$ is 0.01 to 20% by weight and preferably 0.05 to 5% by weight. The culture conditions thereof should be controlled as follows: the culture temperature is 10 to 40° C. and preferably 20 to 35° C.; the quantity of airflow is 0.1 to 2.0 VVM and preferably 0.1 to 1.5 VVM; the rotation speed for stirring is 100 to 800 rpm and preferably 200 to 400 rpm; pH is 3.0 to 10.0 and preferably 4.0 to 9.5.

The separation of a cell body is preferably conducted by centrifugation, the membrane filter procedure and the like. The removal of the low-molecular-weight components such as salts and sugar can be treated with ultrafiltration membranes. Specifically, after the treatment with ultrafiltration membranes, the aqueous solution containing a lipase is concentrated so as to become ½ volume thereof; and then, the same amount of a phosphate buffer as that of the concentrated solution is added thereto. By repeating these procedures once to 5 times, the aqueous solution containing a lipase can be obtained, from which the low-molecular-weight components are removed.

The centrifugation is preferably controlled to 200 to 20,000×g. The pressure applied to the membrane filter is preferably controlled by microfiltration membranes, the filter press and the like to become not more than 3.0 kg/m². In case of enzymes in the cell body, it is preferable that cell breakage thereof is conducted by the homogenizer, Waring blender, the ultrasonic disruption, the French press, the ball mill and the like; then the cell residues are removed by centrifugation, the membrane filter procedure and the like. The rotation speed of the homogenizer for stirring is 500 to 30,000 rpm and preferably 1,000 to 15,000 rpm. The rotation speed of Waring blender is 500 to 10,000 rpm and preferably 1,000 to 5,000 rpm. The time for stirring is 0.5 to 10 minutes and preferably 1 to 5 minutes. It is preferable that the ultrasonic disruption is conducted under the condition of 1 to 50 KHz and more preferably 10 to 20 KHz. It is preferable that the ball mill has glass pellets having the diameter of 0.1 to 0.5 mm.

In the present invention, it is preferable that the aqueous solution containing a lipase is that containing 5 to 30% by weight of lipase as a solid content.

Here, the concentrations of the solid content in the aqueous solution containing a lipase can be determined as Brix. % by using, for example, the sugar content analyzer (Refractometer) (CIS Corporation., Ltd.: BRX-242).

Immediately before the drying process such as spray drying, it is preferable that the aqueous solution containing a lipase is adjusted to pH 6 to 7.5. It is more preferable that it is adjusted to pH 7 or lower and further more preferably to pH 6.5 to 7.0. The pH adjustment can be conducted in any stage before the drying process such as spray drying. The pH of the aqueous solution containing a lipase may be preliminarily adjusted so that pH immediately before the drying process is within the above range. Various alkaline chemicals and acids can be used for the adjustment of pH and alkali metal hydroxides such as sodium hydroxide are preferably used.

In some stage before the drying process, the aqueous solution containing a lipase may be concentrated. The concentration methods are not particularly limited and they include evaporator, flash evaporator, the concentration by ultrafiltration, the concentration by microfiltration, salting out by inorganic salts, precipitation methods with solvents, absorption methods with ion-exchange cellulose and the like, and water absorption methods with water-absorbing gels. Among these, the concentration by ultrafiltration and evaporator are preferable. The module for the concentration by ultrafiltration is preferably a flat membrane or a hollow fiber membrane having a fractioned molecular weight of 3,000 to 100,000 and more preferably 6,000 to 50,000. The materials of the membrane are preferably polyacrylonitrile, polysulfonic and the like.

It is preferable that spray drying is conducted by spray dryers such as nozzle countercurrent flow, disk countercurrent flow, nozzle concurrent flow and disk concurrent flow, and the disk concurrent flow is more preferable. The spray drying is preferably controlled as follows: the rotation speed of the atomizer is 4,000 to 20,000 rpm; and heating is 100 to 200° C. for inlet temperature and 40 to 100° C. for outlet temperature.

Another lipase of component (a) used in the present invention is a lipase derived from *Penicillum* sp. As the lipase, a lipase derived from *Penicillium camemberti*, that is, a 1,3-specific lipase is preferably used. As this powdered lipase, Lipase G "AMANO" 50 sold by AMANO ENZYME Co., Ltd. and the like can be used. The optimal pH of this lipase is 5.0, in particular, the lipase effectively acts between pH 4.5 and 6.0. The optimal temperature of the lipase is 40° C. This powdered lipase is a white to fawn-colored fine powder having no carrier.

In addition to this lipase, a lipase derived from *Penicillium* sp. can be obtained as a powdered material by the method as explained in relation to the above-mentioned lipase derived from *Rhizomucor* sp.

The lipase of component (b) used in the present invention is a lipase derived from *Alcaligenes* sp. As a powdered material of this lipase, Lipase QL and Lipase PL of Meito Sangyo Co., Ltd. and the like can be used.

The properties of Lipase QL are as follows: the molecular weight determined by gel filtration is from 180,000 to 190,000, the isoelectric point is 4.1, the optimal pH is from 7 to 8.5, the optimal temperature is 60° C., the pH stability is from 6 to 10 and the temperature stability is 40° C. or less. The properties of Lipase PL are as follows: the molecular weight determined by gel filtration is from 350,000 to 370,000, the isoelectric point is 4.5, the optimal pH is from 7 to 8.5, the optimal temperature is from 37 to 40° C., the pH stability is from 7 to 10 and the temperature stability is 40° C. or less. Both lipases are a buff yellow fine powder having no carrier. According to the present invention, Lipase QL is preferably used.

In addition to this lipase, a lipase derived from *Alcaligenes* sp. can be obtained as a powdered material by the method as explained in relation to the above-mentioned lipase derived from *Rhizomucor* sp.

Another lipase of component (b) used in the present invention a lipase derived from *Rhizopus* sp. and a lipase derived from *Thermomyces* sp. As the lipase derived from *Rhizopus* sp., a lipase derived from *Rhizopus oryzae* is preferably used. As the powdered material of this lipase, powdered Lipase F-AP15 of AMANO ENZYME Co., Ltd. can be used.

As the lipase derived from *Thermomyces* sp., a lipase derived from *Thermomyces lanuginosus* is preferably used. As the powdered material of this lipase, a powdered material obtained by subjecting lipozyme TL (100 L) of NOVOZYME Japan Co., Ltd. to membrane treatment and then triturating the resultant by spray dry can be used.

The particle diameter of the powdered lipases of components (a) and (b) is optional. However, 90% or more of the lipase powders preferably has a particle diameter of 1 to 100 µm. For example, the particle diameter of the powdered lipase can be determined with Particle Size Distribution Analyzer (LA-500) of HORIBA, Ltd.

According to the present invention, as for the proportion of the powdered lipases of components (a) and (b), the weight ratio of component (a) to component (b) is preferably 1:99 to 99:1. In particular, the weight ratio of (a) the powdered lipase which is a lipase derived from *Rhizomucor* sp. to (b) the powdered lipase which is a lipase derived from *Alcaligenes* sp. is more preferably 60:40 to 98:2, and most preferably 70:30 to 95:5. In addition, the weight ratio of (a) the powdered lipase which is a lipase derived from *Penicillium* sp. to (b) the powdered lipase which is a lipase derived from *Alcaligenes* sp. is more preferably 10:90 to 90:10, and most preferably 70:30 to 30:70. In particular, this combination of these lipases is characterized by extremely wide combination ratio of the two powdered lipases which produces advantageously effects.

The weight ratio of (a) the powdered lipase to (b) the powdered lipase which is a lipase derived from *Rhizopus* sp. is more preferably 10:90 to 70:30, and most preferably 20:80 to 40:60. In addition, the weight ratio of (a) the powdered lipase to (b) the powdered lipase which is a lipase derived from *Thermomyces* sp. is more preferably 10:90 to 90:10, and most preferably 30:70 to 80:20.

The esterification method using the powdered lipase composition of the present invention is explained below.

The compound having at least one alcoholic hydroxyl group in the molecule, which is esterified includes various compounds such as various monoalcohols, polyhydric alcohols, amino alcohols etc. Example of the compound includes short chain, medium chain or long chain, saturated or unsaturated, linear or branched alcohols, polyhydric alcohol such as glycols, glycerin, erythritols. Among these, glycerin is preferred.

On the other hand, examples of the carboxylic acid include short chain, medium chain or long chain, saturated or unsaturated, linear or branched carboxylic acid. These include $C_{6-30}$ fatty acid such as octanoic acid, decanoic acid, lauric acid, myristic acid, palmitic acid, stearic acid, oleic acid, linoleic acid, linolenic acid etc. These carboxylic acids can be used singly or in combination of two or more. Among these, unsaturated fatty acid is preferred, in particular, use of conjugated linoleic acid is preferred.

The esterification can be conducted, for example, under the condition described in Japanese Patent un-examined Publication (KOKAI) Hei 13-169795 and Japanese Patent un-examined Publication (KOKAI) Hei 15-113396. For one example, based on the total weight of substrate, that is, total weight of the compound(s) having alcoholic hydroxyl group and carboxylic acid(s), 0.1 to 2% by weight of the powdered lipase composition according to the present invention is added, and the reaction is conducted at 30 to 60° C. for 24 to 72 hours. In this case, the reaction is preferably conducted while water produced by esterification is removed (dewatering) by reducing pressure of the reaction system. Level of depressurization (degree of reduced pressure) is preferably 1 to 100 hPa, more preferably 1 to 50 hPa, and most preferably 1 to 25 hPa. Within this range, dewatering is more preferably conducted while level of depressurization is increased stepwise. Furthermore, dewatering can be more effectively conducted by blowing nitrogen in dewatering treatment. In case where the powdered lipase which is a lipase derived from *Penicillium* sp. is used, it is preferred that based on the total weight of substrate, 0.1 to 5% by weight of water is preliminarily added and then the reaction is started and then, the reaction is conducted while water produced by esterification is removed.

According to the present invention, extremely high ratio of esterification can be obtained, in particular, triglyceride can be prepared directly from glycerin and carboxylic acid in good yield.

The present invention will be explained in detail by the following Examples.

PREPARATION EXAMPLE 1

The low-molecular-weight components were removed by using the UF module (Asahi Chemical Industry Co., Ltd.: SIP-0013) from a lipase derived from *Rhizomucor miehei* of NOVOZYME Japan Co., Ltd., trade name: Palatase (20000 L), which was dissolved and dispersed in an aqueous solution to obtain an aqueous solution containing a lipase (the concentration of the solid content: 10.6% by weight). Specifically, liquid lipase (Palatase) was treated with ultrafiltration membranes under cooling with ice and concentrated so as to become ½ volume thereof. Then, the same amount of a 0.01M phosphate buffer as that of the concentrated solution was added thereto. The same procedures of ultrafiltration and the addition of a phosphate buffer were conducted three times to the resulting solution to obtain an aqueous solution containing a lipase (the volume ratio: a lipase concentrated solution/buffer=1/1).

The pH of the aqueous solution containing a lipase was adjusted with an aqueous solution of sodium hydroxide to become the pH 6.8 to 6.9.

Then, the solution was sprayed by using a spray dryer (SD-1000: TOKYO RIKAKIKAI CO, LTD) under the conditions of inlet temperature: 130° C., the air content for drying: 0.7 to 1.1 $m^3$/min, and spray pressure: 11 to 12 kpa to obtain lipase powder. The shape of the thus-obtained lipase powder was spherical, 90% by weight or more of the lipase powder has a particle size of 1 to 100 μm and the average particle size thereof was 8.2 μm. The particle size was determined by Particle Size Distribution Analyzer (LA-500) of HORIBA, Ltd. The water content after the dry heat at 105° C. for 1 hour was 7.9% by weight.

The concentration of the solid content in the aqueous solution containing a lipase was determined as Brix. % by using the sugar content analyzer (CIS Co., Ltd.: BRX-242).

EXAMPLE 1

Esterification Reaction Under the Nitrogen Blowing Condition Using Various Lipase or Lipase Composition To reaction vessel with agitator, 10 g of glycerin and 90 g of conjugated linoleic acid were added. To the mixture, the following lipase powder enzyme was added under agitation. Shortly after the resultant was left to stand for 30 minutes while the temperature was kept at about 45° C. in water bath, depressurization was conducted by depressurizing pump. At that time, nitrogen was blown to allow easy production of water.

At first, level of depressurization was kept at about 40 hPa. After 2 to 3 hours, the temperature was gradually increased to about 50° C. After additional 2 to 3 hours, the temperature was increased to about 60° C. Then, this temperature was kept. On the other hand, level of depressurization was gradually increased, finally to about 10 hPa.

If G, or G+QL was used as enzyme, before reaction, water of 2% by weight was added thereto based on total weight of glycerin and conjugated linoleic acid.

The progress of esterification reaction was confirmed by GLC analysis while sampling was conducted as needed. In this case, percentages of unreacted glycerin, MG, DG, TG were determined, and production rate of TG was shown in the following Table-1 and FIG. 1.

Used Lipase

RM (1%): The powdered lipase derived from *Rhizomucor miehei* which belongs to *Rhizomucor* sp., prepared by Preparation Example 1 was singly used. Numeric values shown in parenthesis indicate amount of used lipase. If said numeric value is 1%, it is meant that the amount of use lipase is 1% by weight based on the total weight of glycerin and conjugated linoleic acid (hereinafter, the same).

RM (1%)+QL (0.1%) (present invention): Combination of the powdered lipase derived from *Rhizomucor miehei* which belongs to *Rhizomucor* sp., prepared by Preparation Example 1 and the powdered lipase QL derived from *Alcaligenes* sp., prepared by Meito Sangyo Co., Ltd. was used. The used amount was shown in parenthesis (hereinafter, the same).

G (1%): The powdered lipase G "AMANO" 50 derived from *Penicillium* sp., prepared by AMANO ENZYME Co., Ltd. was singly used.

G (0.7%)+QL (0.3%) (present invention): Combination of the powdered lipase G "AMANO" 50 derived from *Penicillium* sp., prepared by AMANO ENZYME Co., Ltd. and the powdered lipase QL derived from *Alcaligenes* sp., prepared by Meito Sangyo Co., Ltd. was used.

QL (1%): The powdered lipase QL derived from *Alcaligenes* sp., prepared by Meito Sangyo Co., Ltd. was singly used.

TABLE 1

| Reaction time (h) | RM (1%) | RM (1%) + QL (0.1%) | G (1%) | G (0.7%) + QL (0.3%) | QL (1%) |
|---|---|---|---|---|---|
| 0 | 0 | 0 | 0 | 0 | 0 |
| 4 | | | | 14 | 2 |
| 5.5 | | 25 | | | |
| 8 | 26 | | 0 | 28 | |
| 16 | | | | 53 | |
| 20 | 56 | 81 | | 64 | 3 |
| 22 | | | 2 | 69 | |
| 24 | 64 | 85 | | | |
| 28 | 69 | 87 | 3 | | |
| 44 | 75 | 91 | 4 | 87 | 3 |

From the result shown in Table 1, it is found that yield of triglyceride after 44 hours was greatly increased, in particular, from 75% to 91% when a combination of the powdered lipase derived from *Rhizomucor miehei* which belongs to *Rhizomucor* sp. and the powdered lipase QL derived from *Alcaligenes* sp. (RM (1%)+QL (0.1%)) was used in place of singly used powdered lipase derived from *Rhizomucor miehei* which belongs to *Rhizomucor* sp. (RM (1%)). Furthermore, in light of triglyceride production, the time that the triglyceride production reached 75% was over 40 hours in case of RM (1%). On the other hand, in case of RM (1%)+QL (0.1%), the time was half of that of RM (1%), that is, 20 hours.

For those skilled in the art, it was surprising that even if the powdered lipase QL derived from *Alcaligenes* sp. was singly used in an amount of 1%, triglyceride was hardly produced.

On the other hand, for those skilled in the art, it was surprising that even if the powdered lipase G "AMANO" 50 derived from *Penicillium* sp. (G (1%)) or the powdered lipase QL derived from *Alcaligenes* sp. (QL (1%)) was singly used, triglyceride was hardly produced, but if a combination of these lipases (G (0.7%)+QL (0.3%)) was used, the yield of triglyceride after 44 hours was very high, in particular, 87%.

EXAMPLE 2

Esterification Reaction Using RM or Various Lipase Composition

To conduct esterification reaction, the same procedure was conducted as that of Example 1 except that nitrogen gas blowing was not conducted, water was added or not added, and final depressurization levels were those shown in Table-2. Sampling was conducted after 47 hours from starting the reaction, and the production rate of TG was confirmed by GLC analysis. In this case, percentages of unreacted glycerin, MG, DG, TG were determined. The production rate of TG was shown in the following Table-2. In Table-2, in case where the description "water added" does not appear, water did not added. In addition, the numeric values expressed as % in item of Enzyme in Table-2 indicate used amount of lipase. If the numeric value is 1%, used amount of lipase is 1% by weight based on the total weight of glycerin and conjugated linoleic acid. Furthermore, the numeric ratio described in parenthesis in item of Enzyme in Table-2 indicates the weight ratio of various lipase combinations.

Used Lipase

RM: The powdered lipase derived from *Rhizomucor miehei* which belongs to *Rhizomucor* sp., which is the same as that of Example 1.

QL: The powdered lipase QL derived from *Alcaligenes* sp., prepared by Meito Sangyo Co., Ltd., which is the same as that of Example 1.

G: The powdered lipase G "AMANO" 50 derived from *Penicillum* sp., prepared by AMANO ENZYME Co., Ltd., which is the same as that of Example 1.

PL: The powdered lipase QL derived from *Alcaligenes* sp., prepared by Meito Sangyo Co., Ltd.

TL: The powder obtained by subjecting lipozyme TL (100 L) derived from *Thermomyces lanugenousu*, prepared by subjecting NOVOZYME Japan Co., Ltd. to membrane treatment and then spray dry.

F-AP: The powdered lipase F-AP15 derived from *Rhizopus oryzae*, prepared by AMANO ENZYME Co., Ltd.

TABLE 2

| Enzyme | TG % | Depressurization hPa |
|---|---|---|
| RM singly used 1% | 69 | 20 |
| RM + QL (1%, 8:2) | 82 | 19 |
| G + QL (1%, 5:5) water added 2% | 80 | 19 |
| RM + PL (1%, 8:2) | 83 | 17 |
| G + TL (1%, 5:5) water added 1% | 89 | 5 |
| G + F-AP (1%, 3:7) water added 2% | 83 | 3 |
| RM + TL (0.6%, 8:2) | 72 | 16 |

From the result shown in Table-2, it is clear that a combination of the particular lipases (a) and (b) improves esterification ratio.

What is claimed is:

1. A lipase composition consisting essentially of a combination of:
   (a) a powdered lipase which is a lipase derived from *Rhizomucor miehei* or a powdered lipase which is a lipase derived from *Penicillium camemberti*; and
   (b) a powdered lipase which is a lipase derived from *Alcaligenes* sp.;

wherein:
the powdered lipases of (a) and (b) are not supported on carriers; and 90% by weight or more of the powdered lipases have a particle size of 1 to 100 µm.

2. The lipase composition according to claim 1, which is used for esterification.

3. A process for preparing an esterified compound(s), which comprises esterifying a compound(s) having at least one alcoholic hydroxyl group in the molecule, in the presence of the lipase composition according to claim 1, with a carboxylic acid(s).

4. The process according to claim 3, wherein the compound having at least one alcoholic hydroxyl group in the molecule is glycerin.

5. The process according to claim 3, wherein the carboxylic acid is unsaturated fatty acid.

6. The process according to claim 3, wherein the esterification is conducted under the reduced pressure.

7. The lipase composition of claim 1, wherein the powdered lipases have a water content of not more than 10% by weight.

8. The lipase composition of claim 1, wherein the powdered lipases have a water content of from 6.5-8.5% by weight.

9. A lipase composition consisting essentially of a combination of:
(a) a powdered lipase which is a lipase derived from *Rhizomucor miehei* or a powdered lipase which is a lipase derived from *Penicillium camemberti*; and
(b) a powdered lipase which is a lipase derived from *Alcaligenes* sp, and which has a molecular weight determined by gel filtration of from 180,000 to 190,000, an isoelectric point of 4.1, an optimal pH of from 7 to 8.5, an optimal pH temperature of 60° C., and a pH stability of from 6 to 10;
wherein:
the powdered lipases of (a) and (b) are not supported on carriers; and 90% by weight or more of the powdered lipases have a particle size of 1 to 100 µm.

* * * * *